(12) United States Patent
Botich et al.

(10) Patent No.: US 6,540,732 B1
(45) Date of Patent: Apr. 1, 2003

(54) FLUID COLLECTION DEVICE WITH CAPTURED RETRACTABLE NEEDLE

(75) Inventors: Michael J. Botich, Oxnard, CA (US); Thor R. Halseth, Simi Valley, CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 0 days.

(21) Appl. No.: 09/461,267

(22) Filed: Dec. 15, 1999

Related U.S. Application Data

(60) Provisional application No. 60/112,371, filed on Dec. 15, 1998, and provisional application No. 60/144,916, filed on Jul. 21, 1999.

(51) Int. Cl.[7] ............................................... A61B 19/00
(52) U.S. Cl. ...................................... 604/413; 604/507
(58) Field of Search ................................ 604/153, 507, 604/506, 93.01, 110, 264, 255, 246, 533, 538, 403, 411, 412–414, 197, 199, 212–217, 192, 198, 905; 128/912, 917; 141/329, 313; 285/3, 4, 93; 600/562, 566, 567, 573, 574–577, 580

(56) References Cited

U.S. PATENT DOCUMENTS

| | | | | |
|---|---|---|---|---|
| 4,320,769 A | * | 3/1982 | Eichhorn et al. | 128/763 |
| 4,449,539 A | * | 5/1984 | Sarstedt | 128/764 |
| 4,867,172 A | * | 9/1989 | Haber et al. | 128/763 |
| 4,998,927 A | * | 3/1991 | Vaillancourt | 604/283 |
| 5,201,717 A | * | 4/1993 | Wyatt et al. | 604/192 |
| 5,360,012 A | * | 11/1994 | Ebara et al. | 128/764 |
| 5,437,639 A | * | 8/1995 | Malenchek | 604/110 |
| 5,447,495 A | * | 9/1995 | Lynn et al. | 604/49 |
| 5,474,546 A | * | 12/1995 | Ambrisco et al. | 604/411 |
| 5,597,536 A | * | 1/1997 | Mayer | 422/103 |
| 5,899,888 A | * | 5/1999 | Jepson et al. | 604/201 |
| 5,961,472 A | * | 10/1999 | Swendson et al. | 600/573 |

* cited by examiner

Primary Examiner—Brian L. Casler
Assistant Examiner—Cris L. Rodriguez
(74) Attorney, Agent, or Firm—Stephen B. Eland; Dann, Dorfman, Herrell & Skillman

(57) ABSTRACT

A retractable needle fluid transfer device is provided. The device includes a manually operable actuator for affecting retraction. Upon depressing the actuator, a spring displaces the needle rearwardly so that the contaminated needle is enclosed, thereby preventing inadvertent needle sticks. The device includes forward and rearward stops for impeding displacement of the needle after the needle is retracted. A seal prevents contaminants from entering the device after the needle is retracted. A safety sampling access port adapter for obtaining fluid samples from a fluid line is also provided. The sampling adapter includes a first end configured to cooperate with an access port attached to the fluid line. The sampling adapter further includes a collapsible socket configured to cooperate with a fluid container such as a vacuum tube. A needle assembly disposed within the housing of the sampling adapter is operable to pierce the seal on the fluid container. After use, the socket is collapsed to prevent contact with the contaminated needle.

11 Claims, 4 Drawing Sheets

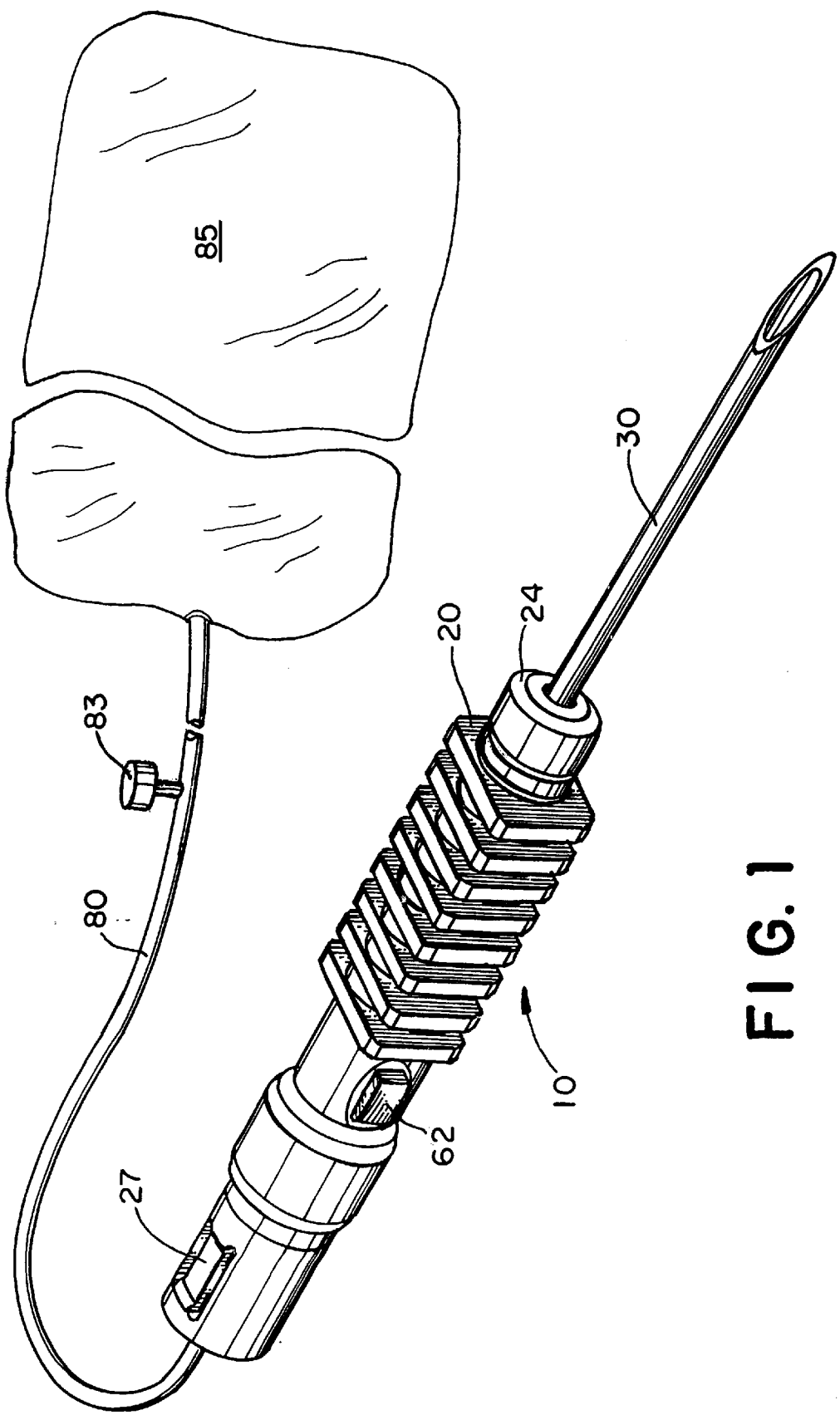

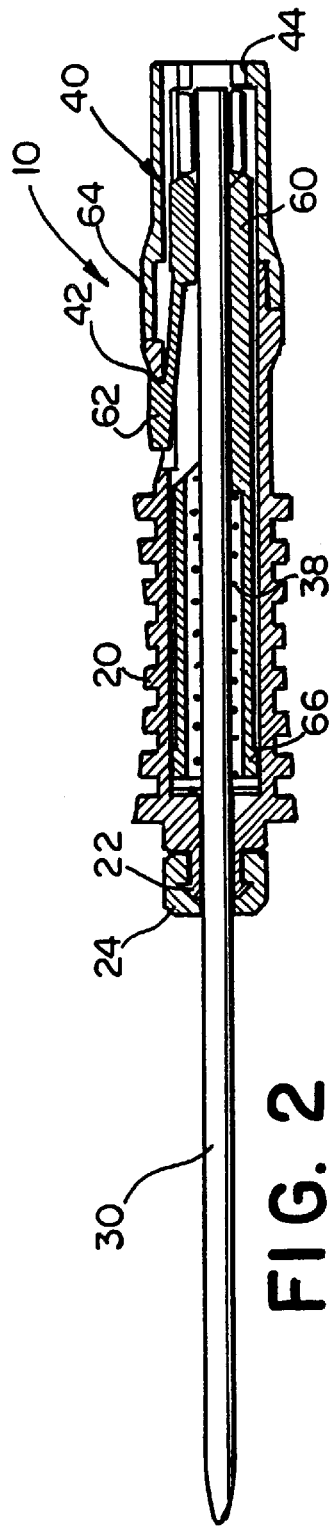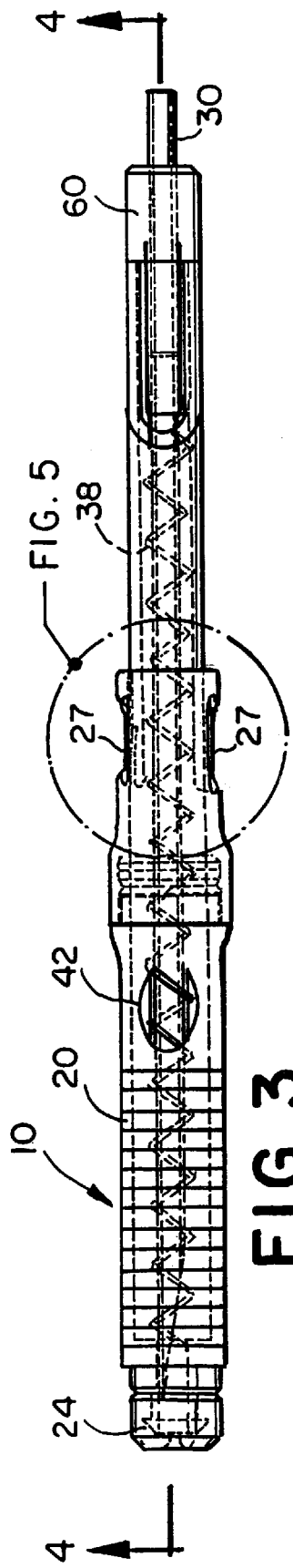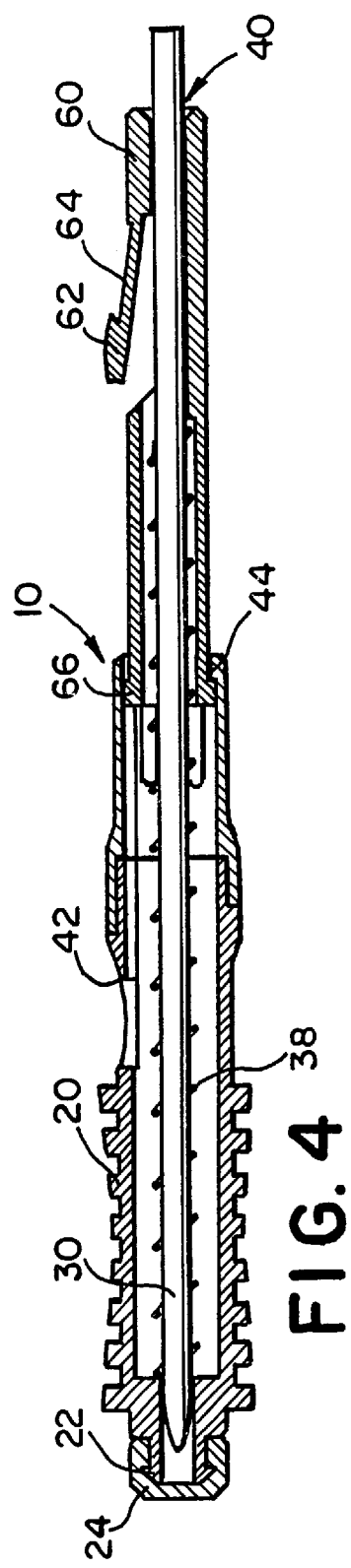

US 6,540,732 B1

FLUID COLLECTION DEVICE WITH CAPTURED RETRACTABLE NEEDLE

This application claims the benefit of Provisional application Ser. No. 60/112,371 filed Dec. 15, 1998 and Ser. No. 60/144,916 filed Jul. 21, 1999.

FIELD OF THE INVENTION

The present invention relates to a fluid transfer device for transferring fluid to or from a patient, and more particularly to a fluid transfer device having a retractable needle.

BACKGROUND OF THE INVENTION

Various types of medical devices employ a needle for piercing the skin of a patient for diagnostic or therapeutic purposes. One such fluid transfer device is a fluid collection device which includes a needle for piercing a blood vessel or other part of the patient to allow a fluid, for example, blood, to be withdrawn from a patient. When the needle is inserted into the patient, blood or other fluid is withdrawn through the needle, for example, into a collection bag. Handling of such needle-bearing medical devices after the needle is withdrawn from the patient can result in transmission of various pathogens, most notably human immune virus (HIV), thereby exposing medical personnel and possibly others to serious or fatal illness due to an inadvertent needle stick or scratch.

After use of a needle-bearing medical device, it is desirable to have an easily usable feature for retracting the needle into a housing to avoid contact with the small volume of contaminated fluid or blood that may remain on or inside the needle. It is further desirable that it be made difficult for personnel to accidentally or intentionally re-extend the needle from within the housing.

Accordingly, there is a need for a fluid transfer device that not only retracts the needle following its use, but that also captures or positively retains the needle in the retracted position within the housing thereafter.

SUMMARY OF THE INVENTION

In light of the foregoing, the present invention provides a medical device having a hollow housing and a needle with a sharpened tip. The needle is operable between an extended and a retracted position. The sharpened tip projects forwardly from the housing in the extended position and the sharpened tip is enclosed within the housing in the retracted position. A biasing element biases the needle toward the retracted position. A needle retainer releasably retains the needle in the extended position. An actuator actuates the needle retainer to release the needle so that the biasing element propels the needle rearwardly toward the retracted position. A rearward stop is operable to retain the needle against continued rearward displacement after the needle is retracted. A forward stop is operable to retain the needle against forward displacement after the needle is retracted. The needle is in fluid communication with a flexible conduit. The flexible conduit is in turn in fluid communication with an expandable reservoir. In this way, fluid flows from the patient, through the needle and into the expandable fluid reservoir. A pierceable seal forms a fluid-tight seal over the forward end of the housing after the needle is displaced into the retracted position.

The present invention also provides a safety sampling access port adapter for obtaining fluid samples in a fluid container having a pierceable seal from a fluid line having an access port with a pierceable fluid seal. The sampling adapter includes a housing having a first end adapted to cooperate with the access port and a collapsible socket. The socket has displaceable walls operable in a first position in which the socket is configured to receive the fluid container and a second position in which the walls are displaced inwardly to limit access to the socket. The device further includes a double-ended needle having a forward end for piercing the seal of the access port and a rearward end projecting into the collapsible socket for piercing the seal of the fluid container.

BRIEF DESCRIPTION OF THE DRAWING

The following detailed description of the preferred embodiments according to the present invention will be better understood when read in conjunction with the accompanying drawings, in which:

FIG. 1 is a perspective view of a retractable needle blood collection device showing the needle in an extended position;

FIG. 2 is a fragmentary side sectional view of the device illustrated in FIG. 1;

FIG. 3 is a fragmentary plan view of the device illustrated in FIG. 2 showing the needle in a retracted position;

FIG. 4 is a fragmentary sectional view of the device illustrated in FIG. 3, take along the line 4—4;

DETAILED DESCRIPTION OF THE PREFERRED EMBODIMENTS

Figure 5:
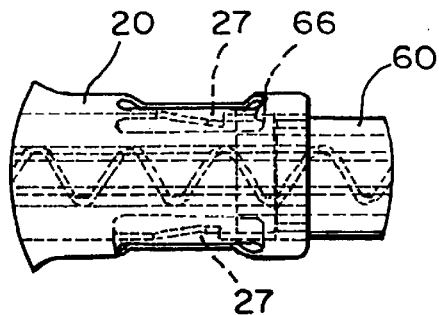
FIG. 5 is a fragmentary view of the portion of the device in FIG. 3 designated 5.

Referring now to FIGS. 1–5 in general and to FIG. 1 specifically, a device for collecting blood is designated generally 10. The device 10 includes a housing 20 and a retractable needle 30 projecting forwardly from the housing. The needle has a sharpened tip operable to pierce a blood vessel of the blood donor. The rearward end of the needle is in fluid communication with an expandable reservoir 85, so that blood flows from the blood donor into the reservoir. As blood flows into the reservoir 85, the reservoir expands to accommodate the blood. After the blood donation is complete, the needle 30 is retracted into the housing 20 to enclose the sharpened tip of the needle to prevent accidental needle sticks.

The device 10 includes a needle assembly 40 slidably displaceable within the housing 20 between a projecting position in which the needle 30 projects forwardly from the housing 20, and a retracted position in which the needle is retracted within the housing. The needle assembly 40 includes a needle tube 60, the insertion needle 30 and a needle retainer 64. The needle 30 is fixedly connected to the needle tube 60 such as by adhesive or alternatively by a press fit or by insert molding. A coil spring 38 biases the needle assembly 40 toward the retracted position. In the projecting position, the needle retainer 64 releasably retains the needle assembly against the rearward bias of the spring 38.

In the present instance, the needle retainer comprises an elongated resilient arm 64 that is integrally formed with the needle tube 60. An actuation button 62 formed on the end of the arm 64 projects into an aperture in the side of the housing 20. The aperture forms a rim 42. Since the button 62 projects through the aperture the button is exposed to the user so that the user can manually actuate the button. A rear shoulder formed on the actuation button engages the rim 42 of the aperture to retain the needle assembly against rearward displacement.

The device 10 further includes forward and rearward stops to limit the retraction of the needle assembly 40 and to prevent re-extension of the needle 30 after retraction. The rearward stop is provided by a flange 66 or enlarged head formed on the forward end of the needle tube 60. The flange 66 projects radially outwardly from the needle tube. The flange 66 cooperates with an annular lip 44 formed at the rearward end of the housing 20. The lip 44 projects radially inwardly into the interior of the housing. The forward stop is provided by a latch 27 formed in the rearward end of the housing 20. The latch 27 is integrally formed with the housing 20 and projects radially inwardly into the interior of the housing. The latch 27 has a tapered forward surface and a rear shoulder substantially perpendicular to the forward surface of the flange 66. As the needle is displaced rearwardly during retraction, the flange 66 engages the tapered portion of the latch 27, displacing the latch radially outwardly. After the needle is retracted, the flange is disposed rearwardly of the latch 27 so that the latch resiliently returns to its original position in which it projects into the interior of the housing. Since the rearward end of the latch forms a square shoulder, displacing the needle forwardly after retraction displaces the flange 66 into engagement with the square shoulder of the latch. The square shoulder on the latch operates as a stop to impede forward displacement of the needle assembly 40 after retraction.

Retraction is actuated by manually depressing the actuation button 62 into the interior of the housing 20 until the actuation button is displaced out of engagement with the rim 42 of the aperture. In response to displacing the actuation button, the arm 64 deforms radially inwardly. Once the actuation button is out of engagement with the aperture, the spring 38 propels the needle assembly 40 rearwardly into the housing.

The resilient arm is biased radially outwardly so that button 62 is biased into engagement with the rim 42 of the aperture in the housing 20 in the latched position. The particular position shown in FIG. 1 is the substantially relaxed position of the arm 64. In this position, the rearward end of button 62 is engaged with the aperture rim 42. Depressing button 62 displaces the button out of engagement with the aperture, so as to be fully within the interior of the housing 20, as shown in FIG. 2. In this way, depressing the button 62 disengages the rearward shoulder from the rim 42 of the aperture in the housing 20 to permit the needle 30 and needle tube 60 to move rearwardly under the urging of spring 38 until needle 30 comes to rest in its retracted position as described below.

In FIG. 3, the needle 30 is in the retracted position with the sharpened end of the needle retracted within the housing. The needle 30 fixed to the needle tube 60 is held in the retracted needle position by the engagement of the latch 27 engaging the forward shoulder on the flange 66 and the rearward shoulder on the flange engaging the lip 44 on the housing 20. Thus engaged, needle 30 is precluded from being easily re-extended or returned to the needle-extended position.

As previously described, the needle 30 is in fluid communication with a flexible tube or fluid line 80 (shown in FIG. 1). The fluid line 80 is a sterile vinyl tube and it is fixedly attached to the rearward end of the needle 30. For this reason, preferably, the rearward end of the needle is blunt rather than being sharpened. The tube is attached to the flexible reservoir 85. The reservoir is a plastic bag of the type generally used with fixed needle non-safety devices used for receiving blood. It may be desirable to include a releasable fitting between the needle and the reservoir 85 so that housing 20 and the retracted needle 30 can be separated from the reservoir and disposed of in a Sharps container.

The device 10 further includes a fluid-tight re-sealable seal 24 mounted on a boss 22 formed on the forward end of the housing. When the needle is disposed in the projecting position, as illustrated in FIG. 2, the needle pierces the seal 24 and the seal forms a fluid tight seal with the needle to prevent contaminants from entering the interior of the housing 20. After the needle is retracted, the seal 24 re-seals the opening from the needle, thereby sealing the forward end of the housing to prevent contaminants from entering the interior of the housing.

Configured as described above, the device operates as follows. The needle 30 is initially located in the projecting position. The medical professional pierces a blood donor's vein so that the needle 30 is in fluid communication with the vein. The blood flows through the needle, through the fluid line 80 and into the reservoir 85. As the blood flows into the reservoir 85, the reservoir expands. After a sufficient amount of blood has been withdrawn, the medical professional withdraws the needle from the patient. The actuation button is then depressed to actuate retraction of the needle. The spring 38 then propels the needle into the housing. Alternatively, the medical professional may actuate retraction prior to withdrawing the needle from the patient. In this way, the needle is enclosed by the housing as soon as it is withdrawn from the patient so that the medical professional is never exposed to the sharpened end of the contaminated needle.

Figure 6:
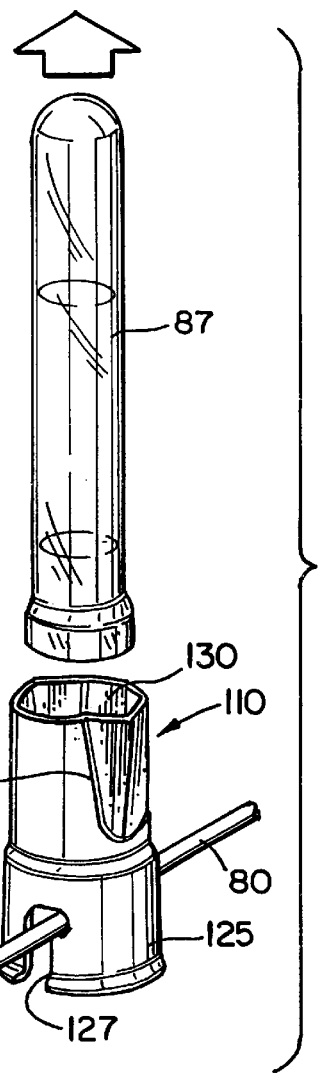
FIG. 6 is a perspective view of a collapsible sampling access port adapter illustrated in combination with a fluid container.
Figure 7:
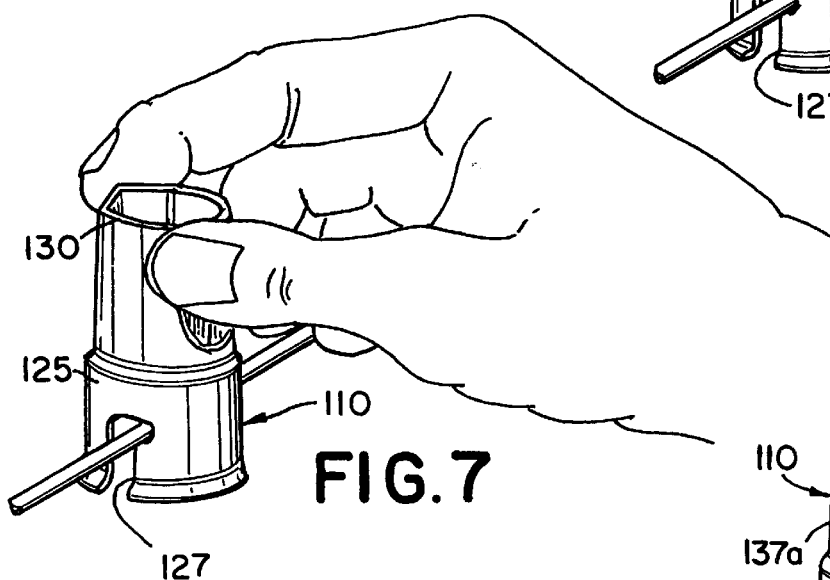
FIG. 7 is a perspective view of an operator collapsing the sampling access port adapter illustrated in FIG. 6.
Figure 8:
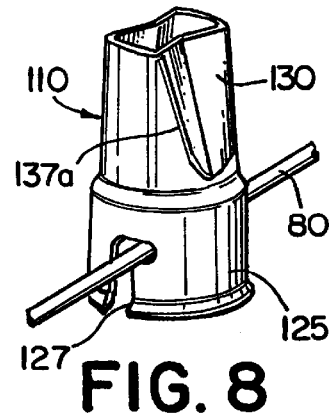
FIG. 8 is a perspective view of the sampling access port adapter illustrated in FIG. 6 showing the adapter in a collapsed position.

Referring now to FIGS. 6–12 generally and to FIG. 6 specifically, a sampling access needle adapter 110 is illustrated. The sampling adapter 110 permits samples to be drawn from the fluid line 80. The sampling adapter 110 includes a double-ended needle assembly 140 for piercing both an access port 83 attached to the fluid line 80 and the seal on a vacuum tube 87. After use, the sampling adapter 110 is substantially permanently collapsible to prevent contact with the contaminated needle assembly 140, as shown in FIG. 8.

Figure 9:
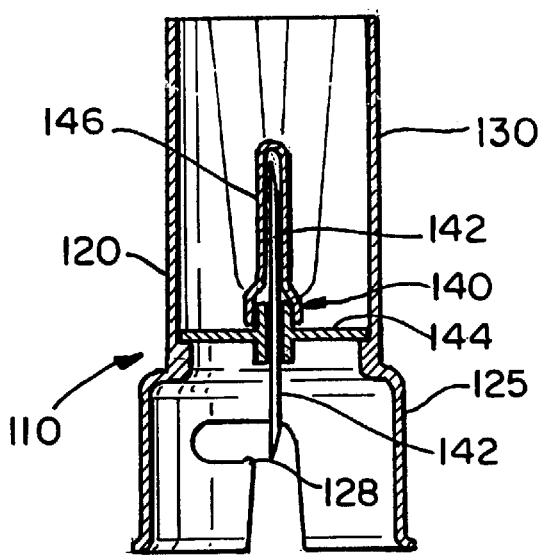
FIG. 9 is a cross-sectional view of the sampling access port adapter illustrated in FIG. 6.

Referring now to FIGS. 6 and 9, the sampling adapter comprises a hollow housing 120 having a lower portion 125 and an upper portion 130. The lower portion 125 is generally cylindrical and has an opening so that the lower portion forms a socket adapted to receive the access port 83 (shown in FIG. 1) on the fluid line 80. The lower socket or access port socket 125 includes a pair of opposing locking slots 127 for connecting the device 110 to the fluid line 80. Each locking slot 127 comprises a first portion intersecting the lower edge of the housing 120 and extending generally parallel to the longitudinal axis of the housing, and a second portion transverse the first portion extending about the circumference of the housing. The width of the locking slot 127 is approximately the same as the diameter of the fluid line 80 so that the locking slot is wide enough to receive the fluid line.

To attach the sampling adapter 110 to the access port 83, the access port is inserted into the lower socket 125 so that the attached fluid line 80 engages the locking slots 127. The access port 83 is inserted deeply enough into the lower socket 125 so that the fluid line 80 engages the end of the first portion of the locking slot 127. The sampling adapter 110 is then rotated about its axis so that the fluid line 80 engages the transverse second portion of the locking slots 127. A detent 128 projects from the intersection of the first and second portions of the locking slots. The detent 128 impedes reverse rotation of the sampling adapter 110 relative to the fluid line 80, thereby operating as a lock to retain the sampling adapter on the access port.

The upper portion 130 is also generally cylindrical and has an opening so that the upper portion forms a socket adapted to receive the vacuum tube 87. The upper portion is formed of a plurality of wall segments 132a, 132b, 134a, 134b. The wall segments are displaceable relative to one another so that the upper portion 130 of the housing 120 can be collapsed after use to prevent contact with the contaminated needle. A plurality of grooves or relief lines 136a, 136b and 137a, 137b formed in the upper portion define the boundaries of the wall segments.

Figure 10:
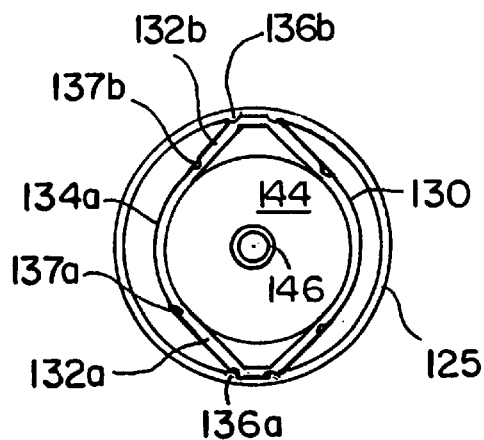
FIG. 10 is a plan view of the sampling access port adapter illustrated in FIG. 9, showing the adapter in an opened position.

Referring to FIG. 10, the upper portion 130 comprises a plurality of wall segments, including a pair of front wall segments 132a, circumscribed by front outer groove 137a and front inner groove 136a, and a pair of opposing rear wall segments 132b circumscribed by rear outer groove 137b and rear inner groove 136a. The upper portion 130 further comprises opposing right side and left side walls 134a, 134b disposed between and connected to the front and rear wall segments 132a, 132b.

The grooves 136a, 136b, 137a, 137b are weakened areas of the upper portion 130 so that when a deformation force is applied to the upper portion, the upper portion will readily deform along the grooves. Accordingly, in response to a deformation force, the wall segments will deform about the grooves. In this way, the grooves form living hinges connecting adjacent wall segments.

Figure 11:
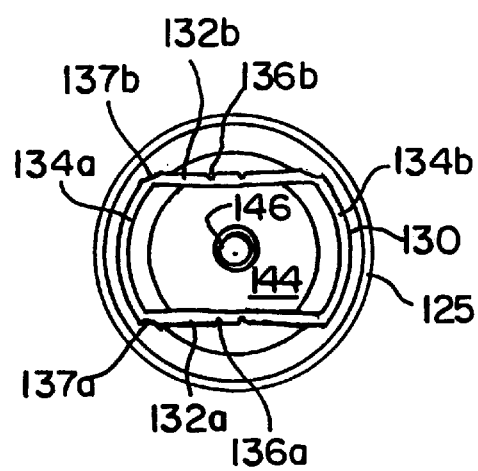
FIG. 11 is a plan view of the sampling access port adapter illustrated in FIG. 10, showing the adapter in an intermediate position.
Figure 12:
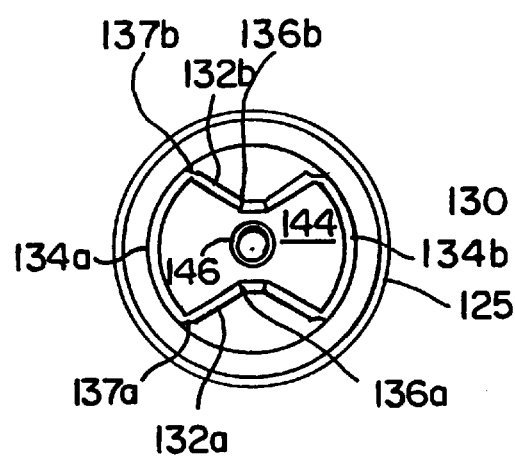
FIG. 12 is a plan view of the sampling access port adapter illustrated in FIG. 10, showing be adapter in a collapsed position.

In FIG. 10, the wall segments are disposed in an opened position in which the upper portion 130 is adapted to receive the vacuum tube 87. The grooves are formed so that the wall segments are biased toward the opened position. As shown in FIGS. 7,11 and 12, after use, the sampling adapter 110 is rendered safe by squeezing the housing 120 to collapse the upper portion 130 by displacing the opposing front and rear sides 132a, 132b radially inwardly toward one another. FIG. 11 illustrates an intermediate position between the opened position illustrated in FIG. 10 and the closed or collapsed position illustrated in FIG. 12. FIG. 11 illustrates an equilibrium position in which the pair of front wall segments 132a are substantially parallel to one another and the pair of rear wall segments 132b are also substantially parallel to one another. The grooves are configured so that the front and rear wall segments 132a, 132b are biased inwardly after the front and rear wall segments are displaced radially inwardly from the equilibrium position illustrated in FIG. 11. Accordingly, when the upper portion 130 is collapsed, the wall segments are biased against displacement toward the opened position illustrated in FIG. 10.

The needle assembly 140 is mounted within the interior of the housing, so that the housing 120 completely encloses the needle assembly. Needle assembly 140 comprises a double-ended needle 142 fixedly attached to a needle hub 144. The needle hub 144 is fixedly connected to be interior of the housing 120 so that the needle 142 is fixed relative to the housing 120. The needle assembly 140 is disposed so that the forward sharpened tip of the double-ended needle projects into the interior of the lower socket 125, and the rearward sharpened tip projects into the interior of the upper socket 130. The needle assembly 140 further comprises a resiliently flexible boot 146 enclosing the rearward sharpened tip of the needle 142.

Configured in this way, the sampling adapter 110 is operable as follows. During fluid transfer, such as blood donation, fluid flows through the fluid line 80. To draw a sample from the fluid line, the medical professional attaches the sampling adapter 110 to the access port 83 (shown in FIG. 1), which has a pierceable seal. The access port is inserted into the lower socket 125 of the sampling adapter 110 so that the needle 142 pierces the access port and the fluid line engages the locking slots 127. The medical professional then rotates the sampling adapter 110 relative to the fluid line 80 to lock the sampling adapter on the access port. The medical professional then inserts a vacuum tube 87 into the upper socket 130 so that the rearward end of the needle 142 pierces the seal of the vacuum tube. In doing so, the vacuum tube collapses the boot 146 enclosing the rearward end of the needle 142 so that the needle pierces the boot. After the vacuum tube 87 is filled with a sufficient quantity of fluid the medical professional removes the vacuum tube from the upper socket 130. The boot 146 is resiliently resealable so that upon withdrawal of the vacuum tube 87, the boot 146 expands to re-enclose and reseal the needle 142 to prevent fluid from leaking out of the fluid line through the needle. If desired, further samples can be drawn into one or more vacuum tubes. After the desired number of samples have been drawn, the last vacuum tube 87 is withdrawn from the upper socket 130. The operator then squeezes the upper socket 130 to deform the upper socket by displacing the wall segments 132a, 132b radially inwardly thereby collapsing the upper socket. Once the upper socket is collapsed, the opening in the upper socket is generally smaller than the finger of the medical professional so that the possibility of an inadvertent needle stick from the contaminated rearward end of the needle 142 is substantially reduced. In addition, since the sampling adapter 110 is locked onto the access port, the front end of the needle 142 is enclosed within the access port thereby preventing inadvertent contact with the front end of the needle.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention.

That which is claimed is:

1. A medical device cooperable with a fluid container having a pierceable seal and a fluid line having an access port with a pierceable fluid seal, comprising:

a housing comprising:

an opening for receiving the access port; and a collapsible socket having displaceable walls being operable in a first position in which the collapsible socket is configured to receive the fluid container and a second position in which the walls are displaced inwardly to limit access to the collapsible socket; and a double-ended needle having a forward end for piercing the seal of the access port and a rearward end projecting into the collapsible socket for piercing the seal of the fluid container.

2. The medical device of claim 1 comprising a connector operable to attach the housing to the fluid line.

3. The medical device of claim 2 comprising a lock operable to impede detachment of the housing from the fluid line after the housing is attached to the fluid line.

4. The medical device of claim 1 wherein in the first position the fluid container is insertable into the collapsible socket, and in the second position the walls impede the insertion of the fluid container into the collapsible socket.

5. A medical device cooperable with a fluid container having a pierceable seal and a fluid line having an access port with a fluid seal, comprising:

a housing comprising:
  a forward end having a socket configured to receive at least a portion of the access port;
  a rearward end comprising a plurality of walls adapted to cooperate with the fluid container; and
  a hinge connecting the walls so that the walls are displaceable relative to one another;

a needle having a rearward end for piercing the seal of the fluid container.

6. The medical device of claim 5 comprising a plurality of hinges connecting the walls.

7. A medical device cooperable with a fluid container having a pierceable seal and a fluid line having an access port with a fluid seal, comprising:

a housing comprising:
  a forward end having an opening adapted to cooperate with the access port;
  a rearward end comprising a plurality of walls adapted to cooperate with the fluid container; and
  a hinge connecting the walls so that the walls are displaceable relative to one another;

a needle having a rearward end for piercing the seal of the fluid container; and a connector operable to attach the housing to the fluid line.

8. The medical device of claim 7 comprising a lock operable to impede detachment of the housing from the fluid line after the housing is attached to the fluid line.

9. A method of sampling fluid from a fluid line having an access port, comprising steps of:

providing a sampler adapter having a needle and a housing having a rearward end configured to receive a fluid container having a pierceable seal;

connecting the sampling adapter to the access port so that the needle is in fluid communication with the fluid line;

piercing the seal of the fluid container with the needle so that the needle is in fluid communication with the container; and substantially permanently deforming the rearward end of the housing to prevent access to the needle.

10. The method of claim 9 wherein the step of substantially permanently deforming the rearward end of the housing comprises collapsing the housing radially inwardly.

11. The method of claim 10 comprising the steps of:

inserting the fluid container into the rearward end of the housing;

drawing a quantity of fluid into the fluid container from the fluid line;

withdrawing the fluid container from the housing; and sealing the end of the needle to prevent fluid from leaking out of the needle.

* * * * *